United States Patent
Wiesbrock et al.

(10) Patent No.: US 8,962,008 B2
(45) Date of Patent: Feb. 24, 2015

(54) HYBRID POLYMERIC MATERIALS FOR MEDICAL APPLICATIONS AND PREPARATION THEREOF

(75) Inventors: Frank Wiesbrock, Graz (AT); Clemens Ebner, Graz (AT); Franz Stelzer, Graz (AT); Annelie-Martina Weinberg, Graz (AT); Klaus-Dieter Kühn, Marburg (DE)

(73) Assignees: Technische Universitat Graz, Graz (AT); Medical University of Graz MUG, Graz (AT); AT&S Austria Technologie & Systemtechnik Aktiengesellschaft, Leoben (AT); Herabus Medical GmbH, Wehrheim (DE)

( * ) Notice: Subject to any disclaimer, the term of this patent is extended or adjusted under 35 U.S.C. 154(b) by 0 days.

(21) Appl. No.: 14/127,255
(22) PCT Filed: Jun. 20, 2012
(86) PCT No.: PCT/AT2012/050083
§ 371 (c)(1),
(2), (4) Date: Feb. 19, 2014
(87) PCT Pub. No.: WO2012/174580
PCT Pub. Date: Dec. 27, 2012

(65) Prior Publication Data
US 2014/0228449 A1 Aug. 14, 2014

(30) Foreign Application Priority Data
Jun. 20, 2011 (EP) .................................. 11170539

(51) Int. Cl.
*A61F 2/00* (2006.01)
*A61K 47/00* (2006.01)
(Continued)

(52) U.S. Cl.
CPC .................. *A61K 47/34* (2013.01); *A61L 27/18* (2013.01); *A61L 31/041* (2013.01); *A61L 31/06* (2013.01);
(Continued)

(58) Field of Classification Search
CPC .......... A61L 27/18; A61L 31/06; A61L 31/14; A61L 31/041; C08G 63/6852; C08G 65/333; C08G 65/325; C08G 63/664; C08J 3/246; C08J 2367/04; C08J 2371/02; C08L 71/02; C08L 67/04; C08L 2205/05; A61K 47/34
USPC .......................... 514/772.1; 525/450; 424/423
See application file for complete search history.

(56) References Cited

U.S. PATENT DOCUMENTS 3,211,752 A   10/1965 Breslow
(Continued)

FOREIGN PATENT DOCUMENTS

EP        0 981 381 B1   2/2007
(Continued)

OTHER PUBLICATIONS

Blanquer et al. ("PCL-Isocyanate: A New, Degradable Macromolecular Synthon for the Synthesis of Polymeric Bioconjugates" in Macromolecular Chemistry and Physics, 2009, 210 1691-1696).*
(Continued)

*Primary Examiner* — Blessing M Fubara
(74) *Attorney, Agent, or Firm* — Norris McLaughlin & Marcus, P.A.

(57) ABSTRACT

The present invention relates to a novel polymeric material with enhanced hydrophilicity for medical use comprising a biocompatible polyester material selected from the group consisting of poly(hydroxyalkanoate)s, poly(lactic acid)s, poly(glycolic acid)s, poly(caprolactone)s and copolymers and blends thereof, wherein the biocompatible polyester material is crosslinked with a functionalized poly(alkylene oxide) having at least two functional groups independently selected from the group consisting of azido-formate and alkanoyl azide. The novel polymeric material with enhanced hydrophilicity is useful as a biocompatible material in a variety of medical applications, including medical implants, bioresorbable implants, tissue engineering, and controlled release.

17 Claims, 2 Drawing Sheets

(51) Int. Cl.
*C08G 63/08* (2006.01)
*A61K 47/34* (2006.01)
*A61L 27/18* (2006.01)
*A61L 31/04* (2006.01)
*A61L 31/06* (2006.01)
*A61L 31/14* (2006.01)
*C08G 63/685* (2006.01)
*C08J 3/24* (2006.01)
*C08G 63/664* (2006.01)
*C08G 65/325* (2006.01)
*C08G 65/333* (2006.01)
*C08L 71/02* (2006.01)

(52) U.S. Cl.
CPC .............. *A61L 31/14* (2013.01); *C08G 63/6852* (2013.01); *C08J 3/246* (2013.01); *C08G 63/664* (2013.01); *C08G 65/325* (2013.01); *C08G 65/333* (2013.01); *C08L 71/02* (2013.01); *C08J 2367/04* (2013.01); *C08J 2371/02* (2013.01); *C08L 2205/05* (2013.01)
USPC .......................... 424/423; 514/772.1; 525/450

(56) References Cited

U.S. PATENT DOCUMENTS

| | | | |
|---|---|---|---|
| 3,284,421 | A | 11/1966 | Breslow |
| 4,968,317 | A | 11/1990 | Törmälä |
| 7,553,923 | B2 | 6/2009 | Williams et al. |
| 2005/0070688 | A1 | 3/2005 | Lewandowski et al. |
| 2009/0325292 | A1 | 12/2009 | Baker et al. |
| 2010/0010621 | A1 | 1/2010 | Klocke |

FOREIGN PATENT DOCUMENTS

| | | |
|---|---|---|
| GB | 1 410 725 | 10/1975 |
| WO | 2004 092247 A1 | 10/2004 |
| WO | WO 2004/092247 A1 * | 10/2004 |
| WO | 2008 071796 A1 | 6/2008 |

OTHER PUBLICATIONS

Xie et al. ("Cyclic Poly(e-caprolactone) Synthesized by Combination of Ring-Opening Polymerization with Ring-Closing Metathesis, Ring Closing Enyne Metathesis, or "Click" Reaction" in Journal of Polymer Science: Part A: Polymer Chemistry, vol. 47, 3022-3033 (2009).*

International Search Report of PCT/AT2012/050083 mailed Sep. 5, 2012.

* cited by examiner

HYBRID POLYMERIC MATERIALS FOR MEDICAL APPLICATIONS AND PREPARATION THEREOF

This application is a 371 of International Patent Application No. PCT/AT2012/050083, filed Jun. 20, 2012, which claims priority of European Patent Application No. 11170539.8, filed Jun. 20, 2011, the entire contents of which patent applications are incorporated herein by reference.

The present invention relates to a polymeric material with enhanced hydrophilicity. for medical use comprising a biocompatible polyester material and to medical devices comprising the polymeric material. The invention also relates to a method for preparing the polymeric material. The novel polymeric material with enhanced hydrophilicity is useful as a biocompatible material in a variety of medical applications, including medical implants, bioresorbable implants, tissue engineering, and controlled release.

Biopolymers, especially biopolyesters, have attracted much interest over the past decades because of their bioresorbability and biocompatibility which renders them interesting candidates as substitutes for conventional plastics or as polymeric biomaterials for medical applications [G.-Q. Chen, Q. Wu, Biomaterials 2005, 26, 6565; S. Philip, T. Keshavarz, I. Roy, J. Chem. Technol. Biotechnol. 2007, 82, 233]. Due to their relatively high price compared to oil-based polymers, the wide spread use of bioplastics in everyday use is still limited; nevertheless there is potential for high-priced products that can find applications in e.g. medicine [G.-C. Chem. Chem. Soc. Rev. 2009, 38, 2434; S. J. Lee, Biotechnol. Bioeng. 1996, 49, 1].

Biocompatible polyester materials are well known in the art. Besides poly(lactic acid) (PLA)s, poly(glycolic acid)s (PGAs), and poly(caprolactone)s (PCLs), poly(hydroxyalkanoate)s (PHAs) have gained importance owing to a plethora of different hydroxyacids that can be incorporated in the respective polymers resulting in an enhanced controllability over mechanical and chemical properties [A. Steinbüchel, H. E. Valentin, FEMS Microbiol. Lett. 1995, 128, 219; R. W. Lenz, R. H. Marchessault, Biomacromolecules 2005, 6, 1].

A general classification of PHAs can be done with respect to the chain length of the monomer units of which the polymer is formed. Monomers of short-chain-length PHAs (scl-PHAs) consist of 3 to 5 carbon atoms, whereas repeating units of medium-chain-length PHAs (mcl-PHAs) contain 6 to 14 carbon atoms [S. J. Lee, Biotechnol. Bioeng. 1996, 49, 1; R. W. Lenz, R. H. Marchessault, Biomacromolecules 2005, 6, 1]. While mcl-PHAs tend to be soft or tacky with low degrees of crystallinity, scl-PHAs are brittle and highly crystalline thermoplasts [W. J. Orts, M. Romansky, J. E. Guillet, Macromolecules 1992, 25, 949; B. Hazer, S. I. Demirel, M. Borcakli, M. S. Eroglu, M. Cakmak, B. Ermann, Polym. Bull. 2001, 46, 389].

To increase the mechanical strength of mcl-PHAs, γ-ray-induced, UV-induced, and chemical crosslinking are known from literature for mcl-PHAs bearing saturated [M. S. Divyashree, T. R. Shamala, Radiat. Phys. Chem. 2009, 78, 147] and unsaturated [B. Hazer, S. I. Demirel, M. Borcakli, M. S. Eroglu, M. Cakmak, B. Ermann, Polym. Bull. 2001, 46, 389; R. D. Ashby, A.-M. Cromwick, T. A. Foglia, Int. J. Biol. Macromol. 1998, 23, 61; A. Dufresne, L. Reche, R. H. Marchessault, Int. J. Biol. Macromol. 2001, 29, 73; S. N. Kim, S. C. Shim, D. Y. Kim, Y. H. Rhee, Y. B. Kim, Macromol. Rapid. Commun. 2001, 22, 1066; M. Schmid, A. Ritter, A. Grubelnik, M. Zinn, Biomacromolecules 2007, 8, 579] side chains.

Modifications of scl-PHAs by chemical crosslinking have only scarcely been performed so far. UV-induced crosslinking of the scl-PHA-member poly(3-hydroxybutyrate-co-3-valerate) PHB-HV in thin films using a fully conjugated bisfunctional azide to yield high crosslinking degrees in short irradiation times was disclosed recently [B. Rupp, C. Ebner, E. Rossegger, C. Slugovc, F. Stelzer, F. Wiesbrock, Green Chem. 2010, 12, 1796].

Another issue especially related to medical applications of PHAs is their hydrophobic character which results in a lower biocompatibility and slow and hardly controllable resorption kinetics in physiological systems. Therefore, numerous attempts have been made to increase the hydrophilicity of hydrophobic PHAs mainly by grafting onto the polymer or introduction of hydrophilic groups [B. Hazer, Energy and Power Engineering 2010, 31]. These reactions either lead to hydrophilic polymers that bear functional groups [D. J. Stigers, G. N. Tew, Biomacromolecules 2003, 4, 193; M. Y. Lee, W. H. Park, Macromol. Chem. Phys. 2000, 201, 2771; M. Y. Lee, S. Y. Cha, W. H. Park, Polymer, 1999, 40, 3787; H. W. Kim, C. W. Chung, Y. H. Rhee, Int. J. Biol. Macromol. 2005, 35, 47; C. W. Chung, H. W. Kim, Y. B. Kim, Y. H. Rhee, Int. J. Biol. Macromol. 2003, 32, 17; J. Babinot, E. Renard, V. Langlois, Macromol. Rapid Commun. 2010, 31, 619; L. Massieu, M. L. Haces, T. Montinel, K. Hernandez-Fonseca, Neurocscience 2003, 120, 335] or form hydrophilic polymer networks [J. Sparks, C. Scholz, Biomacromolecules, 2008, 9, 2091; B. Hazer, R. W. Lenz, B. Cakmakli, M. Borcakli, H. Kocer, Macromol. Chem. Phys. 1999, 200, 1903; S. Domenek, V. Langlois, E. Renard, Polym. Degrad. Stab. 2007, 92, 1384].

Modifications of unsaturated scl- and mcl-PHAs and saturated mcl-PHAs have been performed with hydroxyl-[T. D. Hirt, P. Neuenschwander, U. W. Suter, Macromol. Chem. Phys. 1996, 197, 1609], carboxyl-[D. J. Stigers, G. N. Tew, Biomacromolecules 2003, 4, 193; M. Y. Lee, W. H. Park, Macromol. Chem. Phys. 2000, 201, 2771], and amine-groups [M. Y. Lee, S. Y. Cha, W. H. Park, Polymer, 1999, 40, 3787; J. Sparks, C. Scholz, Biomacromolecules, 2008, 9, 2091] or hydrophilic polymers like poly(ethylene glycol) PEG [B. Hazer, R. W. Lenz, B. Cakmakli, M. Borcakli, H. Kocer, Macromol. Chem. Phys. 1999, 200, 1903; H. W. Kim, C. W. Chung, Y. H. Rhee, Int. J. Biol. Macromol. 2005, 35, 47; C. W. Chung, H. W. Kim, Y. B. Kim, Y. H. Rhee, Int. J. Biol. Macromol. 2003, 32, 17; S. Domenek, V. Langlois, E. Renard, Polym. Degrad. Stab. 2007, 92, 1384; J. Babinot, E. Renard, V. Langlois, Macromol. Rapid Commun. 2010, 31, 619].

In addition, the incorporation of carboxylate ions in the surface of poly(3-hydroxybutyrate-co-3-hydroxyhexanoate) to form a more hydrophilic surface was reported.

EP 0981 381 B1 discloses biocompatible polyhydroxyalkanoate polymers and methods of preparation to remove endotoxin as well as use thereof in a variety of bio-medical in vivo applications, including tissue engineering, wound dressing, drug delivery, and in prosthetics.

U.S. Pat. No. 7,553,923 B2 relates to polyhydroxyalkanoate biopolymers with controlled degradation rates and medical uses and application of these materials, e.g. as implantable medical materials and in drug delivery.

WO 2008071796 A1 discloses a method for the preparation of a medical device element involving poly(ethylene oxide).

US 2005/0070688 A1 discloses hydrophilic, crosslinkable oligomer compositions involving poly(alkylene oxide) groups and articles prepared therefrom, in particular, hydrophilic gel coatings or layers for medical devices.

U.S. Pat. No. 3,284,421 discloses a process of crosslinking polymers with different kinds of azidoformates by means of heat or irradiation.

U.S. Pat. No. 3,211,752 discloses azidoformate crosslinking agents and their use in crosslinking polymers.

A main drawback of known aliphatic polyesters in medical applications is their low hydrophilicity. This is of crucial importance for the swelling behaviour in physiological systems. Surface energies of most polyesters are rather low, indicative of their non-hydrophilic character, resulting in low wettability and too low degradation rates. The low wettability induces low biocompatibility and insufficient interaction between implant material and living tissue. Another drawback in the use of known bioresorbable polyesters is the relatively low controllability of the resorption kinetics leading to a negative impact on medical applications. Due to the bulk erosion of known materials, resorption kinetics are hard to control and can lead to unfavourable and undesirable low or high degradation rates. Low degradation rates are known for PHAs and poly(caprolactone)s.

It is, therefore, an object of the present invention to provide a novel polymeric material for medical use, wherein the material has increased hydrophilicity and enhanced wettability. Another object is to provide a polymeric material having improved swelling behaviour and controllability of resorption kinetics in physiological systems. It is yet another object to provide a biocompatible medical device comprising the polymeric material with enhanced hydrophilicity.

This object is achieved by a polymeric material with increased hydrophilicity for medical use comprising a biocompatible polyester material selected from the group consisting of poly(hydroxyalkanoate)s, poly(lactic acid)s, poly(glycolic acid)s, poly(caprolactone)s and copolymers and blends thereof, wherein the biocompatible polyester material is crosslinked with a functionalized poly(alkylene oxide) having at least two functional groups independently selected from the group consisting of azidoformate and alkanoyl azide.

Surprisingly, it was found that the modification of a biocompatible polyester material with a functionalized poly(alkylene oxide) as defined in the claims results in a novel biocompatible polyester/polyether hybrid material providing significant benefits over the biopolyesters known in the art:

The polymeric material according to the invention has an increased hydrophilicity and wettability in comparison to non-crosslinked biopolyesters. This is of crucial importance for medical applications.

An improved swelling behaviour in an aqueous environment observed for the polymeric material according to the invention. Swelling in physiological systems provides higher biocompatibility and optimum interaction between, e.g. a medical implant manufactured of a polymeric material according to the invention and living tissue or other physiological environments.

In contrast to known biopolyesters, e.g. non-crosslinked PHAs, the polymeric material according to the invention provides a better geometric adaptation of implants and other shaped articles to its environment in in vivo applications.

The swollen surfaces of the polymeric material according to the invention implicate higher surface areas and lead to higher bioresorption rates. The resorption rates of conventional PHAs are generally far too low.

Due to the hybrid material's network structure bioresorption is limited to the swollen surface areas, i.e. biodegradation is based on surface erosion. This important advantage of the novel material provides a higher controllability of resorption kinetics in contrast to bulk erosion.

Several biodegradation pathways are possible. Not only esterases, but also, e.g. amidases, can degrade the polymeric material according to the invention.

The novel hybrid polymeric material comprises two distinct substance classes covalently linked with each other, wherein the biocompatibility of the respective substance is either known or can be easily determined by means of methods known by those skilled in the art, e.g. routine trials.

The present polymeric material shows also great potential for including a wide variety of active pharmaceutical ingredients (APIs), in particular therapeutic, prophylactic and diagnostic agents. APIs can be included in the hybrid polymeric material by post-synthetic impregnation strategies at room or ambient conditions. Thus, degradation of temperature-sensitive APIs and formation of potentially toxic by-products by temperature-induced decomposition and alteration can be avoided. Owing to the polymeric material's network structure, degradation characteristics can be aligned to follow surface erosion. Release of APIs then is strictly controlled by the polymer's degradation. Due to the swelling behaviour of the polymeric material, the APIs will not be released by diffusion, but only concomitant with the degradation of the polymer network. Non-crosslinked or native biopolyesters predominantly follow bulk erosion, such that the aforementioned controlled release of APIs is not possible.

The improved swelling behaviour of the polymeric material according to the invention is demonstrated in the examples below. The results presented in the examples show swelling in aqueous environments. The swelling degrees observed are lower than 2 and, consequently, the mechanical properties are still within the suitable range for medicinal and medical applications; concomitantly, an implant manufactured of the polymeric material fills the allocated sphere. Given the polymeric material's swelling degree of >0 in water (which would be zero for non-crosslinked biopolyesters such as PHAs), a higher wettability and, hence, enhanced interaction of the polymeric material within aqueous based physiological environments, e.g. a mammalian subject, are provided.

BRIEF DESCRIPTION OF THE DRAWINGS

The invention will now be described in greater detail with reference to the drawings, wherein.

The term "subject" as used herein refers to humans or animals. In many aspects, the subject is a human being.

The term "biocompatible" as used herein refers to materials that do not induce a (cyto)toxic or severe immunological response or other undesirable tissue reactions in vivo or in physiological systems.

The term "bioresorbable" refers to a polymer being degraded and resorbed by a biological system under physiological conditions, e.g. by cellular activity in a mammalian or human subject.

The term "hydrophilic" as used herein describes the ability of a polymeric material to absorb water such that swelling and favorable degradation rates in physiological systems occur, while no polymeric material is being dissolved. For use in physiological systems low swelling degrees (SD) are preferred: SD<2.

The terms "biocompatible polyester", "biocompatible poly (ester)", "biopolyester" and "biopoly(ester) as used herein interchangeably refer to a polymer containing ester functional groups in its main chain, wherein the term "biocompatible" has the meaning as defined above. Biopolymers in the form of biopolyesters are well known in the art.

The biocompatible polyesters as used in the present invention for crosslinking with a functionalized poly(alkylene oxide) as defined in the claims are selected from the group consisting of poly(hydroxyalkanoate)s, poly(lactic acid)s, poly(glycolic acid)s and poly(caprolactone)s. Particularly, the poly(caprolactone) is a poly($\epsilon$-caprolactone). In certain embodiments, the poly(lactic acid) PLA is a poly-(L-lactic acid) PLLA or a poly(D-lactic acid) PDLA.

Figure 1:
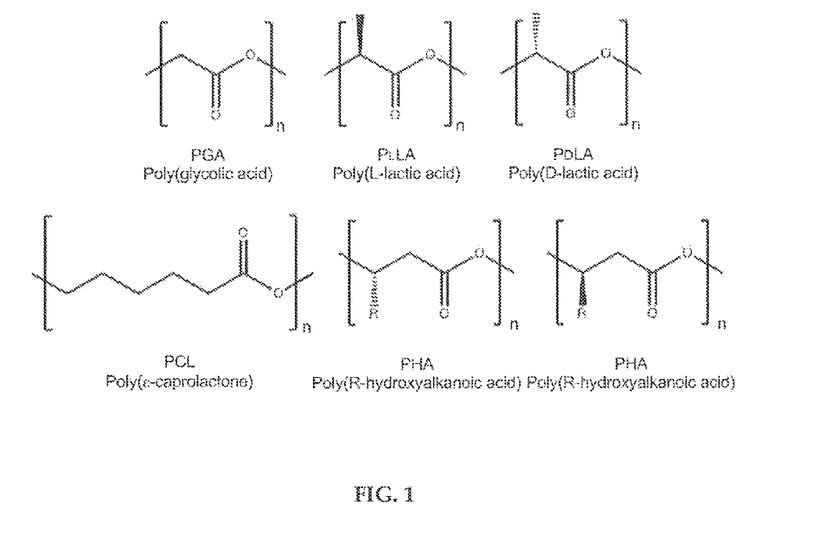
FIG. 1 illustrates chemical structures of preferred biocompatible polyester materials according to the invention.

Poly-(L-lactic acid)s MIAs, poly(glycolic acid)s PGAs, poly(hydroxyalkanoic acid)s PHAs and poly($\epsilon$-caprolactone)s PCLs are useful for medicinal applications due to their mechanical properties, [R. Chandra and R. Rustgi, *Prog. Polym. ScI.* 1998, 23, 1273-1335], their biocompatibility [U.S. Pat. No. 4,968,317; L. G. Griffith, *Acta Mater.* 2000, 48, 263-277], and ease of processing through conventional methods [G. C. Eastmond: Poly($\epsilon$-caprolactone) blends, *Adv. Polym. Sci.* 1999, 149, 59-223]. FIG. 1 illustrates chemical structures of preferred biocompatible polyester materials according to the invention.

In one aspect of the invention, the biocompatible polyester material is a copolymer of the aforementioned biopolyesters. Copolymerization can be used for fine-tuning the targeted properties. For example, the poly(D/L-lactic acid) PDLLA stereocopolymer has higher mechanical stability than pure PLLA and degrades faster [J. Slager and A. J. Domb, *Adv. Drug. Deliver. Rev.* 2003, 55, 549-583]. Poly(L-lactic acid)-co-poly(glycolic acid) degrades nearly 20 times faster than pure PLLA [F. V. Burkersroda, L. Schedl and A. Göpferich, *Biomaterials* 2002, 23, 4221-4231; M. Deng, J. Zhou, G. Chen, D. Burkley, Y. Xu, D. Jamiolkowski and T. Barbolt, *Biomaterials* 2005, 26, 4327-4336]. In similar fashion, irradiation-induced crosslinking lowers the degradation rates [G. J. M. de Koning, H. M. M. van Bilsen, P. J. Lemstra, W. Hazenberg, B. Witholt, H. Preusting, J. G. van der Galien, A. Schirmer and D. Jendrossek, *Polymer* 1994, 35, 2090-2097].

Blending and compounding is a promising approach for tuning the original properties of polymers with the aim to increase the mechanical performance and the bioactivity/biocompatibility of the materials and to align the degradation kinetics with the specific application.

Therefore, in one aspect of the invention, the biocompatible polyester material is a blend of the aforementioned biopolyesters, e.g., blends of PHAs, for example P3HB, P4HB, PHV and the corresponding copolyesters, and/or PLAs, for example PLLA/PDLA/PDLLA and the corresponding copolyesters and/or PGA and/or PCL.

In certain embodiments the biopolyester is a PHA. As already outlined above, this class of substances can be divided into two basic groups according to the chain length of the incorporated monomer units: PHAs with monomers bearing 3-5 carbon atoms are referred to as short-chain-length PHAs (scl-PHAs), whereas PHAs with monomers consisting of 6-14 carbon atoms are called medium-chain-length PHAs (mcl-PHAs).

While mcl-PHAs tend to be soft or tacky with low degrees of crystallinity, scl-PHAs are brittle and highly crystalline thermoplasts, which renders them preferred candidates for medical applications because of their higher mechanical stability and easier processability compared to mcl-PHAs. In a preferred embodiment of the invention, the biocompatible polyester material is a short-chain-length PHA or a blend of short-chain-length PHAs.

In certain preferred embodiments, the biocompatible polyester material is selected from the group consisting of poly (3-hydroxybutyrate) (PHB), poly(3-hydroxybutyrat-co-3-valerate) (PHBV) and blends thereof. Both PHB and PHBV are well-known for their biocompatibility and their suitability for medical applications.

In one specific aspect, the invention relates to a PHB-PEG or PHBV-PEG hybrid polymer network to combine the benefits of crosslinking the well-known biopolyesters PHB and PHBV by incorporation of PEG in order to obtain a hybrid polymer network with enhanced hydrophilicity. These polymer networks can be prepared by reaction of a bisfunctional PEG with PHB or PHBV yielding a material with higher wettability and potentially increased mechanical strength as well as faster and tunable resorption kinetics to meet the requirements needed for medical applications. A significant advantage of the combination of PEG with scl-PHAs like PHB is given by the FDA-approval for PEG, rendering the final degradation products ethylene glycol and 3-hydroxybutyrate not only suitable, but, in the case of 3-hydroxybutyrate, even potentially beneficial for the mammalian body.

Figure 2:
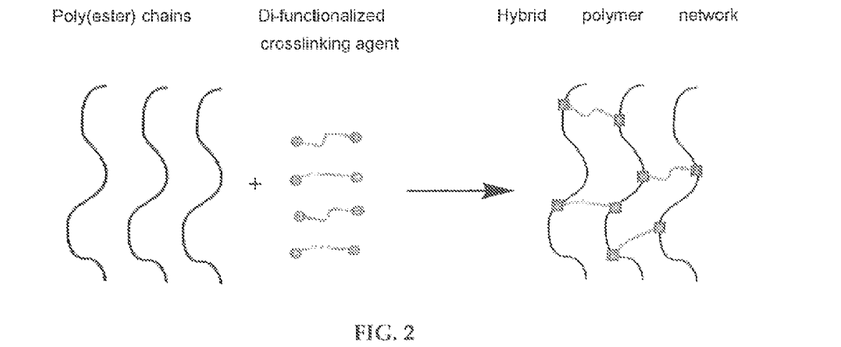
FIG. 2 schematically illustrates the crosslinking of biopolyester chains with di-functionalized poly(alkylene oxide)s as crosslinking agents.

The term "crosslinking" as used herein means the formation of a polymer network, wherein the abovementioned biopolyesters are modified by the reaction with a functionalized poly(alkylene oxide) having at least two functional groups independently selected from the group consisting of azidoformate and alkanoyl azide. The functionalized poly (alkylene oxide) compounds are covalently bound to the biopolyester chains and, hence yield hybrid polymeric networks. FIG. 2 schematically illustrates the crosslinking of biopolyester chains with di-functionalized poly(alkylene oxide)s as crosslinking agents.

Accordingly, a further aspect of the invention relates to a method for preparing a polymeric material with enhanced hydrophilicity according to the invention comprising the steps of
(a) selecting a biocompatible polyester material selected from the group consisting of poly(hydroxyalkanoate)s, poly(lactic acid)s, poly(glycolic acid)s, poly(caprolactone)s and copolymers and blends thereof,
(b) dissolving the biocompatible polyester material in an appropriate solvent for obtaining a polyester material solution,
(c) adding an appropriate amount of a functionalized poly (alkylene oxide) having at least two functional groups independently selected from the group consisting of azidoformate and alkanoyl azide to the polyester material solution, and
(d) crosslinking the biocompatible polyester material with the functionalized poly(alkylene oxide) after removing the solvent and subsequent thermal treatment in inert atmosphere under vacuum.

The method for preparing a polymeric material with enhanced hydrophilicity according to the invention is further described in the examples given below. The solvent used depends on the respective starting substances; selection of an appropriate solvent is known by those skilled in the art. Usually, the solvent is an organic solvent, such as chloroform.

In certain embodiments the functionalized poly(alkylene oxide) has exactly two functional groups independently selected from the group consisting of azidoformate and alkanoyl azide, i.e. a di-functionalized poly(alkylene oxide).

In preferred embodiments the functionalized poly(alkylene oxide) is selected from the group consisting of a compound of formula I herein referred to as bisazidoformate-capped poly(alkylene oxide):

I and a compound of formula II herein referred to as bisalkanoylazide-capped poly(alkylene oxide):

II wherein R in formula I and formula II is independently selected from the groups or combinations of groups consisting of H and $C_2$-$C_{15}$ straight, branched or cyclic alkyl optionally substituted with halogens, preferably —Cl, alkenyl or alkynyl groups, alkaryl groups, heteroalkyl groups, heteroaryl groups, hydroxy groups, thiol groups, disulfides, sulfonates, ether groups, thiol ether groups, ester groups, carboxylic acid groups, amine groups, amide groups, ammonia groups with any non-toxic counter ions, anhydrides, azides [including —$OCON_3$, —$O(CH_2)_mCON_3$, m=1-10], —$NH_2$ and —$NH_3Cl$, and wherein n is an integer between 2 and 15, preferably between 3 and 10.

Examples for optionally substituted $C_1$-$C_2$ alkyl are for example $CH_2X$, $C_2H_4X$ and $C_2H_3X_2$, wherein X is —Cl, —OH, —$OCON_3$, —$O(CH_2)_mCON_3$, —$NH_2$ and —$NH_3Cl$ as defined above. Furthermore, the mentioned amine and amide groups may encompass secondary and tertiary amine groups. Useful examples of ammonia groups with non-toxic-counter ions are —$NH_3$,or —$NRH_2$,(with R being an alkyl group, in particular an alkyl as mentioned above) in combination with a counter anion such as $HCO_3^-$, $Cl^-$, acetate ($CH_3COO^-$), ascorbate, citrate, glutamate, aspartate.

In order to enhance the crosslinking degree and density, poly(alkylene oxide)s bearing more than tow functionalities can be used as crosslinking agents. Consequently, in certain embodiments the functionalized poly(alkylene oxide) has more than two functional groups independently selected from the group consisting of azidoformate and alkanoyl azide.

Preferred examples for functionalized poly(alkylene oxide) having more than two functional groups are so-called star-shaped alkanoylazide or azidoformate-capped poly(alkylene oxide)s. These compounds can be sythesized with 3 to 8 azide functionalities and different chain length of the poly(alkylene oxide) moiety.

These compounds can be purchased from, e.g. Creative PEG works or be synthesized from commercially available (NOF Corporation, Chem Pilots) precursor substances following standard procedures. Branched multi-armed poly (alkylene oxide)s can also be synthesized using, e.g. diepoxy compounds [G. Lapienis and S. Penczek, *J. Polym. Sci. Pol. Chem.* 2004, 42, 1576-1598] and subsequently be functionalized employing standard procedures. Azidoformates: From —OH terminated branched PEG derivatives by reaction with phosgene and subsequent reaction of the resulting chloride with an alkali azide. [S. Monsathaporn and F. Effenberger, *Langmuir* 2004, 20, 10375-10378]. Alkanoylazides: From carboxyl-terminated branched PEG derivatives by chlorination using thionyl chloride and subsequent reaction of the resulting chloride with an alkali azide. [N. Kohler, G. E. Fryxell and M. Zhang, *J. Am. Chem. Soc.* 2004, 126, 7206-7211; T. M. V. D. Pinho e Melo: "Synthesis of Azides" in *Organic Azides: Syntheses and Applications*, 1$^{st}$ edition, S. Brese, K. Banert, Eds., J. Wiley & Sons, New York 2010, p. III/85 f.]

The functionalized poly(alkylene oxide) having more than two functional groups may be selected from the group consisting of a compound of formula III herein referred to as 3-arm star-shaped trisalkanoylazide-capped poly(alkylene oxide):

III a compound of formula IV herein referred to as 4-arm star-shaped tetraalkanoylazide-capped poly(alkylene oxide):

IV a compound of formula V herein referred to as 8-arm star-shaped octaalkanoylazide-capped poly(alkylene oxide):

a compound of formula VI herein referred to as 3-arm star-shaped trisazidoformate-capped poly(alkylene oxide):

a compound of formula VII herein referred to as 4-arm star-shaped tetraazidoformate poly(alkylene oxide):

and a compound of formula VIII herein referred to as 8-arm star-shaped octaazidoformate-capped poly(alkylene oxide):

wherein R in formulas III, IV, V, VI, VII and VIII is independently selected from the groups or combinations of groups consisting of H or $C_2$-$C_{15}$ straight, branched or cyclic alkyl optionally substituted with halogens, preferably —Cl, alkenyl or alkynyl groups, alkaryl groups, heteroalkyl groups, heteroaryl groups, hydroxy groups, thiol groups, disulfides, sulfonates, ether groups, thioleter groups, ester groups, carboxylic acid groups, amine groups, amide groups, amide groups, ammonia groups with any non-toxic counter ions, anhydrides, azides [including —$OCON_3$, —$O(CH_2)_m CON_3$, m=1-10], —$NH_2$ and —$NH_3Cl$, and wherein n is an integer between 2 and 15, preferably between 3 and 10. The same deliberations as above apply.

In certain preferred embodiments R in formulas I, II, III, IV, V, VI, VII and VIII represents hydrogen or —CH3, and preferably hydrogen. In other words, crosslinking agents based on poly(ethylene glycol) (PEG) and poly(propylene oxide) (PPO) are preferred, wherein crosslinking agents based on PEG are particularly preferred.

The polymeric material according to the invention is useful in a great variety of medical applications due to its increased hydrophilicity, its improved swelling behaviour and the concomitant advantages as discussed in detail above. The polymeric material with enhanced hydrophilicity is, therefore, particularly useful in the preparation of a biocompatible medical device.

A further aspect of the invention relates to a biocompatible medical device comprising a polymeric material with enhanced hydrophilicity according to the invention. The invention is useful for manufacturing a great variety of medical devices, including medical implants, bioresorbable implants, tissue engineering devices, and controlled release devices.

In certain embodiments the biocompatible medical device is in the form of a medical implant. Typically the medical implant according to the invention is a bioresorbable medical implant which, after a certain period, is degraded by natural mechanisms occurring within the body. Residence times in mammalian bodies are limited to a maximum duration of 5 years; the hybrid polymeric material described in this invention enables for tailor-made degradation times: depending on their compositions the degradation of a given polyester, which can be in the range from 0.5 to 5 years, can be accelerated by factors of 2 to 10 given the degree of chemical modification with poly(alkylene oxide)s.

In certain embodiments the medical implant is in the form of an orthopaedic implant, in particular a bone implant or a bone replacement. The polymeric material with enhanced hydrophilicity is particularly useful as an implant for bone fracture fixation and for filling bone defects, e.g. adhesive and structural bone fillers. In this context, orthopaedic applications for the bones in the extremities are of primary interest for the polymeric materials according to the invention. Other possible applications are in the field of joint replacements, such as an artificial knee. Moreover, ophthalmologic applications are well conceivable, also in the context of contact lenses and implants for the eye.

Furthermore, the polymeric material with enhanced hydrophilicity according to the invention is also useful for the manufacture of an implant for tissue regeneration, repair and restoration and to improve tissue function in general, wherein subcutaneous implants are particularly preferred. In certain embodiments the medical implant comprising a polymeric material with enhanced hydrophilicity according to the invention is, therefore, in a form selected from the group consisting of osteo-synthethic devices, tissue engineering scaffolds, tissue regeneration devices, tissue replacements, and stents.

The polymeric material according to the invention is useful for including a wide variety of active pharmaceutical ingredients (APIs), in particular therapeutic, prophylactic and diagnostic agents.

APIs can be included in the hybrid polymeric material by post-synthetic impregnation at room or ambient conditions. Thus, degradation of temperature-sensitive APIs and formation of potentially toxic by-products by temperature-induced decomposition and alteration can be avoided. Therefore, a further aspect of the invention relates to a method for including a therapeutic, prophylactic and/or diagnostic agent in a polymeric material comprising the steps of:

(a) selecting a polymeric material with enhanced hydrophilicity according to the invention, (b) swelling the polymeric material in a solution comprising the therapeutic, prophylactic and/or diagnostic agent, and (c) drying the polymeric material.

Alternatively, APIs may also be included in the course of the preparation of the hybrid polymer network by addition of the API to the reaction mixture prior to crosslinking by thermal treatment. The API is then incorporated in the polymer network matrix; release is controlled only by degradation of the polymeric material.

Owing to the polymeric material's network structure, degradation characteristics can be aligned to follow surface erosion. Release of APIs then is strictly controlled by the polymer's degradation. Due to the swelling behaviour of the polymeric material, the APIs will not be released by diffusion, but only concomitant with the degradation of the polymer network. Consequently, in one aspect, the polymeric material with enhanced hydrophilicity according to the invention is also useful in applications relating to controlled release and drug delivery/drug depot.

In one aspect of including APIs, the medical device as described above is in the form of a bioresorbable depot comprising therapeutic, prophylactic and/or diagnostic agents. In another aspect of including APIs, the above-described medical implants may comprise therapeutic, prophylactic and/or diagnostic agents.

Examples of suitable therapeutic and prophylactic agents include, but are not limited to, chemical substances, biomolecules such as proteins, peptides, lipids, nucleic acids, enzymes etc. Antibiotics may be included in order to suppress inflammatory conditions. Integrins may be included near an implant's surface in order to promote cell adhesion. Other therapeutic agents include nutrients and growth factors in order to aid tissue growth and repair.

Further useful examples of therapeutic, prophylactic and diagnostic agents suitable for inclusion into the polymeric material according to the invention are described in, e.g., EP 0 981 381 B1 and US 2010/0010621 A1.

The present invention is further demonstrated and illustrated by the following examples, yet without being restricted thereto.

EXAMPLE 1

Preparation of Hybrid Polymer Networks by Crosslinking the Biopolyester poly(3-hydroxybutyrate-co-3-valerate) (PHBV) with tri(ethyleneglycol)-di-(azidoformate) (DAF) as Network Forming Crosslinking Agent PHBV is shown in formula IX:

DAF is shown in formula X:

Solutions of commercial grade poly(3-hydroxybutyrate-co-3-valerate) PHBV with a valerate content of 18.25% in chloroform were prepared under microwave-assisted heating to 100° C. for 10 min. At room temperature, different amounts of DAF as crosslinking agent ranging from 0 to 50 wt.-% with respect to the polymer mass were added to the solutions. PHBV was purchased from PHB Industrial S/A. PHBV can also be synthesized mainly over ring-opening polymerizations of β-lactones in the presence of catalysts or initiators [A. Le Borgne and N. Spassky, Polymer 1989, 30, 2312-2319; Y. Hori, Y. Takahashi, A. Yamaguchi, T. Nishishita, Macromolecules, 1993, 26, 4388-4390]. DAF was synthesized by reacting tri(ethylene glycol)bis(chloroformate) (purchased from Aldrich) with sodium azide. After thorough mixing the solutions were transferred to hemispheric molds of 12 mm diameter in a solid stainless steel block. Filling was done in two steps to fill up the whole volume preset by the molds. The remaining solvent was evaporated under vacuum at a temperature of 40° C. over night.

The dry hemispherical polymer/crosslinker molds were treated thermally for one hour at a temperature of 180° C. For the quantification of the system's crosslinking ability sol-gel analysis was done in solutions of hot dichloromethane in closed vessels at 100° C. for 10 min under microwave assisted heating. After heating the 0% samples were completely dissolved, whereas already at 10 wt.-% of DAF significant extents of crosslinking were detected. In addition, swelling tests in water and dichloromethane were performed. The crosslinked polymer networks showed significant swelling in dichloromethane and swelling in water, indicating increased hydrophilicity and wettability of the obtained hybrid polymer. The characteristics of the PHB-co-HV samples are summarized in Table 1.

TABLE 1

Characteristics of PHB-co-HV crosslinked with DAF.

| Sample-No. | Amount of DAF/% | Gel Fraction/% | Swelling degree in $H_2O$ | Swelling degree in $CH_2Cl_2$ |
|---|---|---|---|---|
| 1 | 0 | 0 | 0 | n.a* |
| 2 | 10 | 8 | 0.6 | n.a* |
| 3 | 20 | 58 | 0.1 | 9.0 |
| 4 | 30 | 68 | 0.7 | 9.1 |
| 5 | 40 | 69 | 0.6 | 11.9 |
| 6 | 50 | 85 | 0.5 | 14.4 |

*soluble

EXAMPLE 2

Preparation of Hybrid Polymer Networks by Crosslinking the Biopolyester poly(L-lactic acid) PLLA with tri(ethyleneglycol)-di-(azidoformate) DAF as Network Forming Crosslinking Agent PLLA is shown in formula XI:

XI

DAF is shown in formula XII:

XII

Solutions of poly(L-lactic acid) PLLA in chloroform were prepared under microwave-assisted heating to 100° C. for 10 min. At room temperature, different amounts of DAF as crosslinking agent ranging from 0 to 50 wt.-% with respect to the polymer mass were added to the solutions. PLLA was purchased from Aldrich. PLLA can also be synthesized from the monomer's cyclic diester [D. K. Gilding, A. M. Reed, *Polymer* 1979, 20, 1459-1464]. DAF was synthesized by reacting tri(ethylene glycol)bis(chloroformate) (purchased from Aldrich) with sodium azide. After thorough mixing the solutions were transferred to hemispheric molds of 12 mm diameter in a solid stainless steel block. Filling was done in two steps to fill up the whole volume preset by the molds. The remaining solvent was evaporated under vacuum at a temperature of 40° C. over night.

The dry hemispherical polymer/crosslinker molds were treated thermally for one hour at a temperature of 180° C. For the quantification of the system's crosslinking ability sol-gel analysis was done in solutions of hot dichloromethane in closed vessels at 100° C. for 10 min under microwave assisted heating. After heating the 0% samples were completely dissolved whereas already at 10 wt.-% of DAF significant extents of crosslinking were detected. In addition, swelling tests in water and dichloromethane were performed. The crosslinked polymer networks showed significant swelling in dichloromethane and swelling in water, indicating increased hydrophilicity and wettability of the obtained novel hybrid polymer. The results are summarized in Table 2.

TABLE 2

Characteristics of PLLA crosslinked with DAF.

| Sample-No. | Amount of DAF/% | Gel Fraction/% | Swelling degree in $H_2O$ | Swelling degree in $CH_2Cl_2$ |
|---|---|---|---|---|
| 1 | 0 | 0 | 0 | *n.a |
| 2 | 10 | 7 | 0 | *n.a |
| 3 | 20 | 55 | 0.1 | >3.3 |
| 4 | 30 | 59 | 0.19 | >3.6 |
| 5 | 40 | 65 | 0.24 | >3.7 |
| 6 | 50 | 71 | 0.58 | >5.5 |

*soluble

EXAMPLE 3

Preparation of Hybrid Polymer Networks by Crosslinking the Biopolyester poly(hydroxy butyrate) PHB with PEG-600 methanoylbisazide PEG-600 MBA as Network Forming Crosslinking Agent PHB is shown in formula XIII:

XIII

PEG-600 MBA is shown in formula XIV:

XIV

Solutions of poly(hydroxy butyrate) in chloroform were prepared under microwave-assisted heating to 100° C. for 10 min. At room temperature, different amounts of PEG-600 MBA as crosslinking agent ranging from 0 to 50 wt.-% with respect to polymer mass were added to the solutions. PHB was purchased from PHB Industrial S/A. PHB can also be synthesized mainly over ring opening polymerizations of β-lactones in the presence of catalysts or initiators [A. Le Borgne and N. Spassky, *Polymer* 1989, 30, 2312-2319; Y. Hori, Y. Takahashi, A. Yamaguchi, T. Nishishita, *Macromolecules*, 1993, 26, 4388-4390]. PEG-600 MBA was synthesized in a two-step synthesis starting from the carboxylate-terminated PEG-600. The PEG-600 carboxylate was purchased from Aldrich and subjected to chlorination using $SOCl_2$. The resulting chloride was reacted with sodium azide to yield PEG-600 MBA. After thorough mixing the solutions were transferred to hemispheric molds of 12 mm diameter in a solid stainless steel block. Filling was done in two steps to fill up the whole volume preset by the molds. The remaining solvent was evaporated under vacuum at a temperature of 40° C. over night.

The dry hemispherical polymer/crosslinker molds were treated thermally for one hour at a temperature of 180° C. For the quantification of the system's crosslinking ability sol-gel analysis was done in solutions of hot dichloromethane in closed vessels at 100° C. for 10 min under microwave assisted heating. After heating the 0% samples were completely dissolved whereas already at 25 wt.-% of PEG-600 BA significant extents of crosslinking were detected. In addition, swelling tests in water and dichloromethane were performed. The crosslinked polymer networks showed significant swelling in dichloromethane and swelling in water (approx. 0.5 with 50 wt.-% of PEG-600 BA), indicating increased hydrophilicity and wettability of the obtained novel hybrid polymer. The results are summarized in Table 3.

TABLE 3

Characteristics of PHB crosslinked with PEG-600 MBA.

| Sample-No. | Amount of DAF/% | Gel Fraction/% | Swelling degree in $H_2O$ |
|---|---|---|---|
| 1 | 0 | 0 | 0 |
| 2 | 10 | 5 | 0.5 |
| 3 | 25 | 45 | 0.4 |
| 4 | 50 | 40 | 0.6 |

EXAMPLE 4

Determination of Swelling Degrees

The crosslinked samples as well as a native polymer reference were dried, weighed (referred to as $m_{dry}$), and allowed to swell to maximum swelling degrees. The adsorbed solvent was removed from the surface and the samples were weighed again (referred to as $m_{swollen}$). The swelling degree (SD) was calculated according to the formula $SD = 100\% * (m_{swollen} - m_{dry})/m_{dry}$.

EXAMPLE 5

Post-Synthetic Inclusion of (Organic) Compounds in the Hybrid Polymer Networks According to the Invention

Figure 3:
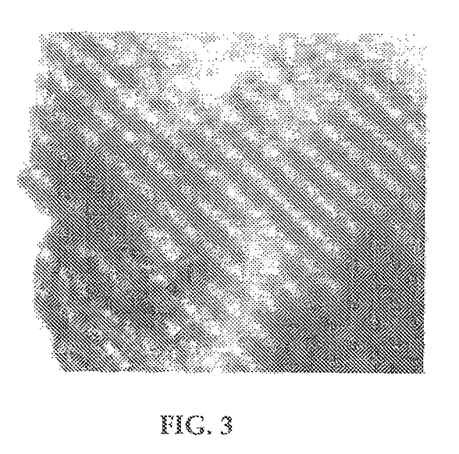
FIG. 3 shows an image of a hybrid polymer network in water with included Eosin Y dye.

Eosin Y was chosen as model compound. A dried PEG-crosslinked PLA network (with 10 wt.-% content of DAF as crosslinking agent—see Example 2 above) was swollen in an Eosin Y/dichloromethane/ethanol solution. The dye diffused into the polymer network during 36 h. The swollen sample was subsequently dried under vacuum and washed with water in order to remove surface-adsorbed dye. Due to lower swelling in water, no occluded Eosin Y was released from non-degraded polymer networks. FIG. 3 shows an image of a hybrid polymer network in water with included Eosin Y dye. These results indicate that the present polymer network can be used as delivery system for APIs, e.g. antibiotics, providing several benefits that originate from the hybrid polymer's nature.

The invention claimed is:

1. A polymeric material with enhanced hydrophilicity for medical use comprising a biocompatible polyester material selected from the group consisting of poly(hydroxyalkanoate)s, poly(lactic acid)s, poly(glycolic acid)s, poly(caprolactone)s and copolymers and blends thereof, wherein the biocompatible polyester material is crosslinked with a functionalized poly(alkylene oxide) having at least two functional groups independently selected from the group consisting of azidoformate and alkanoyl azide.

2. The polymeric material with enhanced hydrophilicity according to claim 1, wherein the functionalized poly(alkylene oxide) has two functional groups independently selected from the group consisting of azidoformate and alkanoyl azide.

3. The polymeric material with enhanced hydrophilicity according to claim 2, wherein the functionalized poly(alkylene oxide) is selected from the group consisting of a compound of formula (I)

and a compound of formula (II)

wherein R in formula (I) and formula (II) is independently selected from the groups or combinations of groups consisting of H and $C_2$-$C_{15}$ straight, branched or cyclic alkyl optionally substituted with halogens, alkenyl or alkynyl groups, alkaryl groups, heteroalkyl groups, heteroaryl groups, hydroxy groups, thiol groups, disulfides, sulfonates, ether groups, thiol ether groups, ester groups, carboxylic acid groups, amine groups, amide groups, ammonia groups with any non-toxic counter ions, anhydrides, azides, $NH_2$ and —$NH_3CL$, and wherein n is an integer between 2 and 15.

4. The polymeric material with enhanced hydrophilicity according to claim 1, wherein the functionalized poly(alkylene oxide) has more than two functional groups independently selected from the group consisting of azidoformate and alkanoyl azide.

5. The polymeric material with enhanced hydrophilicity according to claim 4, wherein the functionalized poly(alkylene oxide) is selected from the group consisting of a compound of formula (III), a compound of formula (IV), a compound of formula (V), a compound of formula (VI), a compound of formula (VII)

a compound of formula (VIII)

wherein R is independently selected from the groups or combinations of groups consisting of H and $C_2$-$C_{15}$ straight, branched or cyclic alkyl optionally substituted with halogens, alkenyl or alkynyl groups, alkaryl groups, heteroalkyl groups, heteroaryl groups, hydroxy groups, thiol groups, disulfides, sulfonates, ether groups, thioleter groups, ester groups, carboxylic acid groups, amine groups, amide groups, amide groups, ammonia groups with any non-toxic counter ions, anhydrides, azides —$NH_2$ and —$NH_3Cl$, and wherein n is an integer between 2 and 15.

6. The polymeric material with enhanced hydrophilicity according to claim 3, wherein R represents hydrogen or —$CH_3$.

7. The polymeric material with enhanced hydrophilicity according to claim 1, wherein the biocompatible polyester material is a short-chain-length poly(hydroxyalkanoate) or a blend of short-chain-length poly(hydroxyalkanoate)s.

8. The polymeric material with enhanced hydrophilicity according to claim 7, wherein the biocompatible polyester material is selected from the group consisting of poly(3-hydroxybutyrate), poly(3-hydroxybutyrate-co-3-valerate) and blends thereof.

9. A method of preparing a biocompatible medical device comprising incorporating a polymeric material with enhanced hydrophilicity according to claim 1.

10. A biocompatible medical device comprising a polymeric material with enhanced hydrophilicity according to claim 1.

11. The biocompatible medical device according to claim 10, wherein the device is in the form of a medical implant.

12. The biocompatible medical device according to claim 11, wherein the medical implant is in the form of an orthopaedic implant.

13. The biocompatible medical device according to claim 11, wherein the medical implant is in a form selected from the group consisting of osteosynthetic devices, tissue engineering scaffolds, tissue regeneration devices, tissue replacements, and stents.

14. The biocompatible medical device according to claim 11, further comprising therapeutic and/or diagnostic agents.

15. The biocompatible medical device according to claim 10, wherein the device is in the form of a bioresorbable depot comprising therapeutic and/or diagnostic agents.

16. A method for preparing a polymeric material with enhanced hydrophilicity according to claim 1, said method comprising the steps of:
(a) selecting a biocompatible polyester material selected from the group consisting of poly(hydroxyalkanoate)s, poly(lactic acid)s, poly(glycolic acid)s, poly(caprolactone)s and copolymers and blends thereof, (b) dissolving the biocompatible polyester material in an appropriate solvent for obtaining a polyester material solution, (c) adding an appropriate amount of a functionalized poly(alkylene oxide) having at least two functional groups independently selected from the group consisting of azidoformate and alkanoyl azide to the polyester material solution, and (d) crosslinking the biocompatible polyester material with the functionalized poly(alkylene oxide) after removing the solvent and subsequent thermal treatment in inert atmosphere under vacuum.

17. A method for including a therapeutic and/or diagnostic agent in a polymeric material comprising the steps of:

(a) selecting a polymeric material with enhanced hydrophilicity according to claim 1, (b) swelling the polymeric material in a solution comprising the therapeutic and/or diagnostic agent, and (c) drying the polymeric material.

\* \* \* \* \*

UNITED STATES PATENT AND TRADEMARK OFFICE
CERTIFICATE OF CORRECTION

Page 1 of 1

PATENT NO. : 8,962,008 B2
APPLICATION NO. : 14/127255
DATED : February 24, 2015
INVENTOR(S) : Wiesbrock et al.

It is certified that error appears in the above-identified patent and that said Letters Patent is hereby corrected as shown below:

In the Specification:

Column 1, line 30, "G.-C˙ Chem. Chem." -- should read -- G.C˙ Chen, Chem. --.

Column 2, line 25, "Macromol." -- should read -- *Macromol.* --.

Column 5, line 22, "MIAs" -- should read -- P$_L$LAs --.

In the Claims:

Column 16, line 42, "NH$_2$" -- should read -- -NH$_2$ --.

Signed and Sealed this
Twelfth Day of July, 2016

Michelle K. Lee
*Director of the United States Patent and Trademark Office*